(12) United States Patent
Jones

(10) Patent No.: US 9,849,074 B2
(45) Date of Patent: Dec. 26, 2017

(54) SUNSCREEN COMPOSITION

(75) Inventor: Debra Louise Jones, Selby (GB)

(73) Assignee: CRODA INTERNATIONAL PLC, East Yorkshire (GB)

( * ) Notice: Subject to any disclaimer, the term of this patent is extended or adjusted under 35 U.S.C. 154(b) by 0 days.

(21) Appl. No.: 13/120,110

(22) PCT Filed: Sep. 18, 2009

(86) PCT No.: PCT/GB2009/002220
§ 371 (c)(1),
(2), (4) Date: Mar. 21, 2011

(87) PCT Pub. No.: WO2010/034969
PCT Pub. Date: Apr. 1, 2010

(65) Prior Publication Data
US 2011/0171148 A1    Jul. 14, 2011

(30) Foreign Application Priority Data
Sep. 25, 2008 (GB) .................................. 0817598.6

(51) Int. Cl.
*A61K 8/81* (2006.01)
*A61Q 17/04* (2006.01)
*A61K 8/29* (2006.01)
*B82Y 5/00* (2011.01)

(52) U.S. Cl.
CPC .............. *A61K 8/8182* (2013.01); *A61K 8/29* (2013.01); *A61Q 17/04* (2013.01); *B82Y 5/00* (2013.01); *A61K 2800/413* (2013.01)

(58) Field of Classification Search
None
See application file for complete search history.

(56) References Cited

U.S. PATENT DOCUMENTS

| 5,188,831 A * | 2/1993 | Nicoll et al. .................. 424/401 |
| 6,436,377 B1 * | 8/2002 | Hansenne et al. .............. 424/59 |
| 2003/0147830 A1 * | 8/2003 | Phillips et al. ............ 424/70.14 |
| 2006/0275247 A1 * | 12/2006 | Heiman et al. ................. 424/74 |
| 2008/0299057 A1 * | 12/2008 | Lin ........................ A61K 8/044 424/59 |

FOREIGN PATENT DOCUMENTS

| EP | 1083184 | 3/2001 |
| JP | 2004/059484 | 2/2004 |
| WO | 99/24007 | 5/1999 |
| WO | 01/17488 | 3/2001 |
| WO | 02/067884 | 9/2002 |
| WO | 02/067885 | 9/2002 |

OTHER PUBLICATIONS

"Hydrotriticum PVP", Croda Chemicals, Mar. 1, 1999, pp. 1-3.*
International Search Report dated Oct. 29, 2010 for PCT/GB2009/002220.
"Hydrotriticum PVP" Croda Chemicals, Mar. 1, 1999, pp. 1-3.
"Products Sun Protection: Unititamer T-40", Induchem, Apr. 21, 2008.
"Unititamer T-40", Induchem, Jul. 1, 2009.
"Croda Launches Sunscreen Enhancer", Happi Household and Personal Products Industry, Oct. 7, 2008.
"Aim Higher SolPerForm 100", Croda, Sep. 30, 2010.
"Personal Care Compositions Providing High UVA/UVB Light Protection and Radical Scavenging Effect", IP.com Journal, May 5, 2009.

* cited by examiner

*Primary Examiner* — Melissa Fisher
(74) *Attorney, Agent, or Firm* — RatnerPrestia

(57) ABSTRACT

A composition contains at least one sunscreen and a protein-PVP copolymer. The sunscreen may be organic and/or inorganic, particularly titanium dioxide. The protein-PVP copolymer improves the effectiveness of the sunscreen, resulting in increased SPF values of the composition.

16 Claims, No Drawings

SUNSCREEN COMPOSITION

CROSS REFERENCE TO RELATED APPLICATION

This application is the National Phase application of International Application No. PCT/GB2009/002220, filed Sep. 18, 2009, which designates the United States and was published in English. This application, in its entirety, is incorporated herein by reference.

FIELD OF INVENTION

The present invention relates to a composition comprising at least one sunscreen and a protein-polyvinylpyrrolidone copolymer, a method of making thereof, and in particular to the use of a protein-polyvinylpyrrolidone copolymer to enhance the effectiveness of at least one sunscreen.

BACKGROUND

Due to the increased awareness of the link between ultraviolet (UV) light and skin cancer, there has been a requirement for enhanced ultraviolet light protection in sunscreen products and in everyday skincare and cosmetics products.

There are two basic types of sunscreens, namely inorganic and organic UV absorbers or attenuators. Examples of inorganic sunscreens include metal oxides such as titanium dioxide, zinc oxide and iron oxide. A wide range of organic sunscreens have been used such as p-methoxy cinnamic acid esters, salicylic acid esters, p-amino benzoic acid esters, benzophenone derivatives, derivatives of dibenzoyl methane and esters of 2-cyanoacrylic acid.

The effectiveness of a sunscreen composition or end-use product can be determined by measuring the sun protection factor (SPF). High SPF values can be obtained by increasing the concentration of sunscreens in the formulation, however this will increase the cost, may lead to reduced aesthetic properties such as skin feel and appearance, and/or increased irritancy when applied to the skin.

Thus, there is a need for a material which when incorporated into a sunscreen composition or end-use product exhibits enhanced UV absorption or attenuation properties with inorganic and/or organic sunscreens. The enhancement of the UV absorption properties of inorganic sunscreens can be particularly challenging. There is also a need for such a material to be effective at low concentrations, and a requirement that the use thereof does not detrimentally affect the skin feel of the composition.

Polyvinylpyrrolidone (PVP) polymers and copolymers are well known and have been used in a variety of applications.

SUMMARY OF THE INVENTION

We have surprisingly discovered that the use of a protein-polyvinylpyrrolidone (PVP) copolymer overcomes or significantly reduces at least one of the aforementioned problems.

Accordingly, the present invention provides a composition comprising at least one sunscreen and a protein-PVP copolymer.

The invention also provides an emulsion comprising an oil phase comprising at least one sunscreen, and an aqueous phase comprising a protein-PVP copolymer.

The invention further provides the use of a protein-PVP copolymer to improve the effectiveness of at least one sunscreen.

The amount of protein-PVP copolymer in a composition according to the present invention is suitably in the range from 0.01 to 10%, preferably 0.05 to 5%, more preferably 0.1 to 2%, particularly 0.2 to 1.0%, and especially 0.3 to 0.5%, by weight based on the total weight of the composition.

The amount of sunscreen in a composition according to the present invention is suitably in the range from 1 to 40%, preferably 3 to 30%, more preferably 4 to 20%, particularly 5 to 15%, and especially 6 to 10%, by weight based on the total weight of the composition.

The composition described herein may be in the form of an alcoholic solution or dispersion, preferably containing alcohol in the range from 40 to 90%, more preferably 50 to 80%, particularly 55 to 75%, and especially 60 to 70% by weight of the total composition. Ethanol is preferred, particularly denatured ethanol. The alcoholic composition is particularly suitable for use as a sprayable sunscreen. The advantages of a sprayable composition include coverage of a large surface area in a short period of time, and the cooling effect that can be obtained by evaporation of solvent after the composition has been sprayed onto the surface of the skin. In one preferred embodiment, the composition is in the form of an emulsion (or dispersion), such as an oil-in-water or water-in-oil emulsion, particularly an oil-in-water emulsion.

The oil phase of the emulsion will preferably mainly be an emollient oil of the type used in personal care or cosmetic products. The emollient can and usually will be an oily material which is preferably liquid at ambient temperature. Alternatively, it can be solid at ambient temperature, in which case in bulk it will usually be a waxy solid, provided it is liquid at an elevated temperature at which it can be included in and emulsified in the composition.

Suitable normally liquid emollient oils include non-polar oils, for example mineral or paraffin, especially isoparaffin, oils, such as that sold by Croda as Arlamol™ HD; or medium polarity oils, for example vegetable ester oils such as jojoba oil, vegetable glyceride oils, animal glyceride oils, such as that sold by Croda as Estol™ 3603 (caprylic/capric triglyceride), synthetic oils, for example synthetic ester oils, such as isopropyl palmitate and those sold by Croda as Estol™ 1512 and Arlamol™ DOA, ether oils, particularly of two fatty e.g. C8 to C18 alkyl residues, such as that sold by Cognis as Cetiol OE (dicaprylether), guerbet alcohols such as that sold by Cognis as Eutanol G (octyl dodecanol), or silicone oils, such as dimethicone oil such as those sold by Dow Corning as DC200, cyclomethicone oil, or silicones having polyoxyalkylene side chains to improve their hydrophilicity; or highly polar oils including alkoxylate emollients for example fatty alcohol propoxylates such as that sold by Croda as Arlamol™ E (propoxylated stearyl alcohol).

Mixtures of emollients, including liquid and solid materials, can and often will be used. In some cases solid emollients may dissolve wholly or partly in liquid emollients, or in combination the freezing point of the mixture may be suitably low. Where the emollient composition is a solid (such as fatty alcohols) at ambient temperature, the resulting dispersion may technically not be an emulsion (although in most cases the precise phase of the oily disperse phase cannot readily be determined) but such dispersions behave as if they were true emulsions and the term emulsion is used herein to include such compositions.

The concentration of the oil phase may vary widely. The amount of the oil phase in the emulsion is preferably in the range from 1 to 90%, more preferably 2 to 70%, particularly 5 to 50%, and especially 10 to 35%, by weight based on the total weight of the composition.

The amount of the aqueous phase in the emulsion is preferably in the range from 10 to 99%, more preferably 30 to 98%, particularly 50 to 95%, and especially 65 to 90%, by weight based on the total weight of the composition.

A wide range of emulsifiers may be employed, particularly one or more non-ionic emulsifier(s). Suitable emulsifiers include conventional non-ionic oil-in-water emulsifier surfactants such as alkoxylate emulsifiers and surfactants that can be derived from natural materials such as fatty acid esters, ethers, hemi-acetals or acetals of polyhydroxylic compounds or a fatty acid amide which is N-substituted with the residue of a polyhydroxylic compound. The specific nature of the emulsifier surfactant used in any particular instance depends on the type of emulsion being made, particularly the amount and nature of the oil being emulsified and the total desired level of emulsifier.

The concentration of emulsifier in the emulsion is preferably in the range from 0.1 to 20%, more preferably 0.5 to 15%, particularly 1 to 10%, and especially 2 to 7%, by weight based on the total weight of the composition.

The emulsions of the invention can be made by generally conventional emulsification and mixing methods. Typical methods for producing oil-in-water emulsions include direct emulsification, whereby the oil phase is added to the aqueous continuous phase. It is desirable to either heat the aqueous phase usually above about 60° C., e.g. to about 80 to 85° C., or to subject the aqueous phase to high intensity mixing at lower, e.g. at about ambient, temperature. Vigorous mixing and the use of moderately elevated temperatures can be combined if desired. The heating and/or high intensity mixing can be carried out before, during or after addition of the oil phase.

The emulsions can also be made by inverse emulsification methods, for example whereby the aqueous phase is added and mixed into the oil phase to form a water-in-oil emulsion. Aqueous phase addition is continued until the system inverts to form an oil-in-water emulsion. Plainly a substantial amount of aqueous phase will generally be needed to effect inversion and so this method is not likely to be used for high oil phase content emulsions. Vigorous mixing and the use of moderately elevated temperatures can be combined if desired. The heating and/or high intensity mixing can be carried out during or after addition of the aqueous phase and before during or after inversion.

The protein-PVP copolymer used in the present invention is suitably produced by reacting protein with vinylpyrrolidone, preferably by a free radical polymerization process known in the art.

The ratio of protein to vinylpyrrolidone reacted together to form the protein-PVP copolymer (or ratio of protein to PVP present in the copolymer) is suitably in the range from 2 to 98:2 to 98%, preferably 5 to 70:30 to 95%, more preferably 10 to 50:50 to 90%, particularly 15 to 30:70 to 85%, and especially 20 to 25:75 to 80% by weight.

It is preferred that the protein component is capable of forming a solution in water or other suitable solvent or co-solvent (such as alcohol, propylene glycol, or polyethylene glycol) in order to enable reaction with vinylpyrrolidone to occur.

The protein starting material may be derived from either animal or vegetable sources, or by fermentation. Examples of proteins which are currently used in cosmetic formulations and which can be used as the protein component of the copolymer include collagen, elastin, keratin, casein, wheat protein, potato protein, soya protein and/or silk protein. Wheat protein and/or potato protein are particularly preferred, and especially wheat protein.

The term "protein" is used herein to include both native and hydrolysed proteins, and thus comprises proteins properly so-called and polypeptides, peptides and peptones, since the latter can all be categorised as hydrolysed proteins. Hydrolysed proteins are preferred (which are probably more correctly referred to as polypeptides), and may for example be produced by acid, alkali, and/or enzyme hydrolysis of native proteins. Hydrolysed wheat proteins are particularly preferred. Chemically modified proteins and/or hydrolysed proteins may also be employed, for example whereby the protein has been covalently reacted with a functional group, for example with a silane.

The molecular weight (weight average) of the protein component starting material may vary over a wide range, such as for example in the range from 300 to 500,000 Daltons.

In one preferred embodiment, the molecular weight (weight average) of the protein component starting material is suitably in the range from 300 to 20,000, preferably 500 to 10,000, more preferably 1,000 to 5,000, particularly 1,500 to 3,000, and especially 1,800 to 2,200 Daltons.

In an alternative preferred embodiment, the molecular weight (weight average) of the protein component starting material is suitably in the range from 10,000 to 500,000, preferably 30,000 to 200,000, more preferably 50,000 to 150,000, particularly 60,000 to 100,000, and especially 70,000 to 90,000 Daltons.

One preferred hydrolysed protein suitably comprises on average in the range from 3 to 3,000, preferably 5 to 1,000, more preferably 8 to 500, particularly 12 to 100 and especially 15 to 30 amino acids.

The molecular weight (weight average) of the protein-PVP copolymer used in the present invention is preferably in the range from 1,000 to 1,000,000, more preferably 5,000 to 500,000, particularly 10,000 to 200,000, and especially 15,000 to 100,000 Daltons.

In one preferred embodiment, the molecular weight (weight average) of the protein-PVP copolymer is suitably in the range from 15,000 to 90,000, preferably 20,000 to 75,000, more preferably 25,000 to 60,000, particularly 30,000 to 50,000, and especially 35,000 to 45,000 Daltons.

The molecular weight of the protein starting material and protein-PVP copolymer can be determined by size exclusion chromatography as described herein.

The protein-PVP copolymer is preferably present in the aqueous phase of an emulsion according to the present invention. Thus, the aqueous phase of an emulsion suitably comprises in the range from 0.01 to 10%, preferably 0.5 to 5%, more preferably 0.1 to 2%, particularly 0.2 to 1%, and especially 0.3 to 0.5%, by weight of protein-PVP copolymer based on the total weight of the composition.

The inorganic and/or organic sunscreen(s) may be present in the oil and/or aqueous phase of an emulsion. Particularly enhanced SPF values have been observed when the inorganic and/or organic sunscreen(s) are present in the oil phase.

Thus in a preferred embodiment, the oil phase of an emulsion according to the present invention suitably comprises in the range from 1 to 30%, preferably 2 to 25%, more preferably 3 to 18%, particularly 4 to 12%, and especially 5 to 8%, by weight of sunscreen based on the total weight of the composition.

Whether the inorganic sunscreen is present in the oil and/or aqueous phase of an emulsion depends upon, for example, whether hydrophilic or hydrophobic metal oxide is used, and/or whether the metal oxide is initially dispersed in water or oil prior to forming the emulsion.

Particularly enhanced SPF values have been observed when the metal oxide is present in the oil phase. Thus in a preferred embodiment, the oil phase of an emulsion according to the present invention suitably comprises in the range from 1 to 30%, preferably 2 to 20%, more preferably 3 to 15%, particularly 4 to 12%, and especially 5 to 8%, by weight of metal oxide based on the total weight of the composition.

In one embodiment, the aqueous phase of an emulsion preferably comprises in the range from 0 to 10%, more preferably less than 5%, particularly less than 2%, and especially less than 1%, by weight of metal oxide based on the total weight of the composition.

Preferably the metal oxide used in the present invention comprises an oxide of titanium, zinc and/or iron, more preferably is titanium dioxide and/or zinc oxide, and particularly titanium dioxide.

The average primary particle size of the particles of metal oxide is preferably less than 200 nm, and where the particles are substantially spherical then this size will be taken to represent the diameter. However, non-spherical particles may also be used and in such cases the average primary particle size refers to the largest dimension. The average primary particle size relates to particles of metal oxide which are not aggregated. Frequently, the primary particles consist of single crystals but may also comprise several crystals fused together.

The average primary particle size of the metal oxide particles is preferably in the range from 5 to 150 nm, and more preferably 10 to 100 nm when they are substantially spherical. For titanium dioxide particles having an acicular shape, the average largest dimension of the primary particles is preferably less than 150 nm, and more preferably in the range from 20 to 100 nm. The titanium dioxide particles are suitably acicular in shape and preferably have a mean ratio of largest dimension (length) to shortest dimension (width) in the range from 2.0 to 10.0:1, more preferably 3.0 to 8.0, particularly 4.0 to 6.5, and especially 4.5 to 5.5:1. The third axis of the acicular titanium dioxide particles (or depth) is preferably approximately the same dimensions as the width.

In one preferred embodiment, the mean length by number of the acicular primary titanium dioxide particles is suitably in the range from 50 to 90 nm, preferably 55 to 77 nm, more preferably 55 to 73 nm, particularly 60 to 70 nm, and especially 60 to 65 nm. The mean width by number of the particles is suitably in the range from 5 to 20 nm, preferably 8 to 19 nm, more preferably 10 to 18 nm, particularly 12 to 17 nm, and especially 14 to 16 nm. The size of the primary particles can be suitably measured using electron microscopy. The size of a particle can be determined by measuring the length and width of a particle selected from a photographic image obtained by using a transmission electron microscope.

When the metal oxide is zinc oxide, the particles suitably have an average primary particle size in the range from 30 to 100 nm, and preferably 60 to 90 nm.

The particles of metal oxide may comprise substantially pure metal oxide, but may also carry an inorganic coating. For example, particles of titanium dioxide can be coated with oxides of other elements such as oxides of aluminium, zirconium or silicon, preferably alumina and/or silica. When present, the preferred amount of inorganic coating is in the range 4 to 20%, more preferably 5 to 15%, by weight, calculated with respect to the weight of metal oxide core particles.

In one embodiment, the metal oxide particles are hydrophobic. The metal oxide particles may be rendered hydrophobic, for example, by application of a hydrophobic coating on the surface of the metal oxide particles. The hydrophobicity of the particles can be determined by pressing a disc of metal oxide powder, and measuring the contact angle of a drop of water placed thereon, by standard techniques known in the art. The contact angle of a hydrophobic metal oxide is preferably greater than 50°.

Generally, the metal oxide particles are treated with a water-repellent material in order to render them hydrophobic. Suitable, normally organic, water-repellent materials include fatty acids, preferably fatty acids containing 10 to 20 carbon atoms, such as lauric acid, stearic acid and isostearic acid, salts of the above fatty acids such as sodium salts and aluminium salts, fatty alcohols, such as stearyl alcohol, and silicones such as polydimethylsiloxane and substituted polydimethylsiloxanes and reactive silicones such as methylhydrosiloxane polymers and copolymers. The hydrophobic treatment can be applied using any conventional process. In addition to the water-repellent coating, the metal oxide particles may also carry an inorganic coating as described above.

Generally, the particles are treated with up to 20% by weight of the water-repellent material, calculated with respect to the coated or uncoated core particles, as appropriate, and preferably in the range from 0.05 to 3% by weight of water-repellent material, calculated with respect to coated or uncoated core particles.

The metal oxide may be incorporated into a composition according to the present invention in powder form, but preferably pre-dispersions are employed. Particularly high SPF values have been obtained in compositions according to the present invention by using metal oxide dispersions.

By dispersion is meant a true dispersion, i.e. where the solid particles are stable to aggregation. The particles in the dispersion are relatively uniformly dispersed and resistant to settling out on standing, but if some settling out does occur, the particles can be easily redispersed by simple agitation.

The dispersion suitably contains greater than 25%, preferably greater than 30%, more preferably greater than 35%, particularly greater than 40%, and especially greater than 45% by weight of particles of metal oxide, particularly titanium dioxide, based on the total weight of the dispersion. Generally it is difficult to produce dispersions containing greater than 70% by weight of particles of metal oxide.

The dispersing medium may be water or an organic medium such as any of the aforementioned emollient oils. An organic medium is preferred. A useful organic medium is a liquid oil such as vegetable oils, e.g. fatty acid glycerides, fatty acid esters and fatty alcohols. The organic medium may be a silicone oil or a siloxane fluid, especially a cyclic oligomeric dialkylsiloxane, such as the cyclic pentamer of dimethylsiloxane known as cyclomethicone. Alternative materials include dimethylsiloxane linear oligomers or polymers having a suitable fluidity and phenyltris(trimethylsiloxy)silane (also known as phenyltrimethicone).

Examples of suitable organic media include non-polar materials such as C13-C14 isoparaffin, isohexadecane, paraffinum liquidum (mineral oil), squalane, squalene, hydrogenated polyisobutene, and polydecene; and polar materials such as C12-C15 alkyl benzoate, caprylic/capric triglyceride, cetearyl isononanoate, ethylhexyl isostearate, ethylhexyl palmitate, isononyl isononanoate, isopropyl isostearate, isopropyl myristate, isostearyl isostearate, isostearyl neopentanoate, octyldodecanol, pentaerythrityl tetraisostearate, PPG-15 stearyl ether, triethylhexyl triglyceride, dicaprylyl carbonate, ethylhexyl stearate, helianthus annus (sunflower) seed oil, isopropyl palmitate, and octyldodecyl neopentanoate.

The dispersions used in the present invention may also contain a dispersing agent in order to improve the properties thereof. The dispersing agent is suitably present in the range from 1 to 30%, preferably 2 to 20%, more preferably 9 to 20%, particularly 11 to 17%, and especially 13 to 15% by weight based on the total weight of metal oxide, particularly titanium dioxide, particles.

A wide range of commercially available dispersing agents may be employed. Polyhydroxystearic acid is a particularly preferred dispersing agent in organic media, and acrylic polymers or copolymers in aqueous media.

The metal oxide dispersions are preferably prepared by milling with a particulate grinding medium. Generally, the dispersions are pre-mixed before milling using a high speed stirrer, but, in an alternative process, the dispersing medium is added to the mill initially and then the metal oxide and the dispersing agent co-added to the dispersing medium subsequently. After milling has been carried out for the required time the dispersion is separated from the grinding medium by screening through a narrow gap.

One preferred metal oxide dispersion used in the present invention comprises particulate titanium dioxide suitably having a median volume particle diameter (equivalent spherical diameter corresponding to 50% of the volume of all the particles, read on the cumulative distribution curve relating volume % to the diameter of the particles—often referred to as the "D(v,0.5)" value)), measured as herein described, in the range from 24 to 42 nm, preferably 27 to 39 nm, more preferably 29 to 37 nm, particularly 31 to 35 nm, and especially 32 to 34 nm.

The size distribution of the titanium dioxide particles in dispersion can also be an important parameter in obtaining a composition having the required properties. In a preferred embodiment suitably less than 10% by volume of titanium dioxide particles have a volume diameter of more than 13 nm, preferably more than 11 nm, more preferably more than 10 nm, particularly more than 9 nm, and especially more than 8 nm below the median volume particle diameter. In addition, suitably less than 16% by volume of titanium dioxide particles have a volume diameter of more than 11 nm, preferably more than 9 nm, more preferably more than 8 nm, particularly more than 7 nm, and especially more than 6 nm below the median volume particle diameter. Further, suitably less than 30% by volume of titanium dioxide particles have a volume diameter of more than 7 nm, preferably more than 6 nm, more preferably more than 5 nm, particularly more than 4 nm, and especially more than 3 nm below the median volume particle diameter.

Also, suitably more than 90% by volume of titanium dioxide particles have a volume diameter of less than 30 nm, preferably less than 27 nm, more preferably less than 25 nm, particularly less than 23 nm, and especially less than 21 nm above the median volume particle diameter. In addition, suitably more than 84% by volume of titanium dioxide particles have a volume diameter of less than 19 nm, preferably less than 18 nm, more preferably less than 17 nm, particularly less than 16 nm, and especially less than 15 nm above the median volume particle diameter. Further, suitably more than 70% by volume of titanium dioxide particles have a volume diameter of less than 8 nm, preferably less than 7 nm, more preferably less than 6 nm, particularly less than 5 nm, and especially less than 4 nm above the median volume particle diameter.

Suitable organic UV absorbers for use in the present invention are selected from the group consisting of butyl methoxydibenzoylmethane (avobenzone), benzophenone-3 (oxybenzone), 4-methylbenzylidene camphor (enzacamene), benzophenone-4 (sulisobenzone), bis-ethylhexyloxyphenol methoxyphenyl triazine (bemotrizinol), diethylamino hydroxybenzoyl hexyl benzoate, diethylhexyl butamido triazone, disodium phenyl dibenzimidazole tetrasulfonate, drometrizole trisiloxane, ethylhexyl dimethyl PABA (padimate O), ethylhexyl methoxycinnamate (octinoxate), ethylhexyl salicylate (octisalate), ethylhexyl triazone, homosalate, isoamyl p-methoxycinnamate (amiloxate), isopropyl methoxycinnamate, menthyl anthranilate (meradimate), methylene bis-benzotriazolyl tetramethylbutylphenol (bisoctrizole), octocrylene, PABA (aminobenzoic acid), phenylbenzimidazole sulfonic acid (ensulizole), terephthalylidene dicamphor sulfonic acid, and mixtures thereof.

In a preferred embodiment, oil soluble organic UV absorbers are employed, suitably those selected from the group consisting of butyl methoxydibenzoylmethane (avobenzone), benzophenone-3 (oxybenzone), 4-methylbenzylidene camphor (enzacamene), bis-ethylhexyloxyphenol methoxyphenyl triazine (bemotrizinol), diethylamino hydroxybenzoyl hexyl benzoate, diethylhexyl butamido triazone, drometrizole trisiloxane, ethylhexyl dimethyl PABA (padimate O), ethylhexyl methoxycinnamate (octinoxate), ethylhexyl salicylate (octisalate), ethylhexyl triazone, homosalate, isoamyl p-methoxycinnamate (amiloxate), isopropyl methoxycinnamate, menthyl anthranilate (meradimate), octocrylene, and mixtures thereof.

Preferred oil soluble organic UV absorbers are selected from the group consisting of butyl methoxydibenzoylmethane (avobenzone), bis-ethylhexyloxyphenol methoxyphenyl triazine (bemotrizinol), ethylhexyl methoxycinnamate (octinoxate), ethylhexyl salicylate (octisalate), ethylhexyl triazone, octocrylene, and mixtures thereof. Particularly preferred are those selected from the group consisting of butyl methoxydibenzoylmethane (avobenzone), ethylhexyl methoxycinnamate (octinoxate), octocrylene, and mixtures thereof, and especially ethylhexyl methoxycinnamate (octinoxate).

Thus, the oil phase of an emulsion according to the present invention suitably comprises in the range from 0 to 25%, preferably 1 to 20%, more preferably 2 to 16%, particularly 3 to 12%, and especially 4 to 10%, by weight of organic sunscreen based on the total weight of the composition.

Many other components normally used in personal care or cosmetic compositions or end-use products may be included in the compositions according to the present invention. These components may be oil soluble, water soluble or non-soluble. Examples of such materials include:

(i) preservatives such as those based on parabens (alkyl esters of 4-hydroxybenzoic acid), phenoxyethanol, substituted ureas and hydantoin derivatives e.g. those sold commercially under the trade names Germaben II Nipaguard BPX and Nipaguard DMDMH, when used usually in a concentration of from 0.5 to 2% by weight based on the total weight of the composition;

(ii) perfumes, when used typically at a concentration of from 0.1 to 10% more usually up to about 5% and particularly up to about 2%, by weight based on the total weight of the composition;

(iii) humectants or solvents such as alcohols, polyols such as glycerol and polyethylene glycols, when used typically at a concentration of from 1 to 10% by weight based on the total weight of the composition;

(iv) alpha hydroxy acids such as glycolic, citric, lactic, malic, tartaric acids and their esters; self-tanning agents such as dihydroxyacetone;

(v) antimicrobial, particularly anti-acne components such as salicylic acid;

(vi) vitamins and their precursors including: (a) Vitamin A, e.g. as retinyl palmitate and other tretinoin precursor molecules, (b) Vitamin B, e.g. as panthenol and its derivatives, (c) Vitamin C, e.g. as ascorbic acid and its derivatives, (d) Vitamin E, e.g. as tocopheryl acetate, (e) Vitamin F e.g. as polyunsaturated fatty acid esters such as gamma-linolenic acid esters;

(vii) skin care agents such as ceramides either as natural materials or functional mimics of natural ceramides;

(viii) natural phospholipids, e.g. lecithin;

(ix) vesicle-containing formulations;

(x) botanical extracts with beneficial skin care properties;

(xi) skin whiteners such as dioic acid, kojic acid, arbutin and similar materials;

(xii) skin repair compounds actives such as Allantoin and similar series;

(xiii) caffeine and similar compounds;

(xiv) cooling additives such as menthol or camphor;

(xv) insect repellents such as N,N-diethyl-3-methylbenzamide (DEET) and citrus or eucalyptus oils;

(xvi) essential oils; and (xvii) pigments, including microtine pigments, particularly oxides and silicates, e.g. iron oxide, particularly coated iron oxides, and/or titanium dioxide, and ceramic materials such as boron nitride, or other solid components, such as are used in make up and cosmetics, to give suspoemulsions, typically used in an amount of from about 1 to about 15%, but usually at least about 5% and particularly about 10% by weight based on the total weight of the composition.

The composition according to the present invention suitably has an in vitro Sun Protection Factor (SPF), measured as herein described, of greater than 10, preferably greater than 15, more preferably in the range from 20 to 100, particularly 25 to 70, and especially 30 to 60.

The increase in the SPF value due to the presence of a protein-PVP copolymer in a composition according to the present invention is suitably greater than 20%, preferably greater than 30%, more preferably in the range from 35 to 100%, particularly 40 to 85%, and especially 45 to 80%. These values are calculated with respect to the SPF value of the same sunscreen composition except that it contains no protein-PVP copolymer.

A particularly surprising feature of the present invention is that the above mentioned SPF increases can be achieved at low concentrations, for example at 0.4% by weight of the protein-PVP copolymer, based on the total weight of the composition.

The increase in the SPF value observed is suitably greater than 5%, preferably greater than 8%, more preferably in the range from 10 to 25%, particularly 11 to 20%, and especially 12 to 18% per 0.1% by weight unit of protein-PVP copolymer present in the composition.

Similar in vivo SPF values and increases thereof, as described above for in vitro SPF, could also be obtained.

The compositions according to the present invention also possess good body and skin feel, showing no significant loss of skin feel properties due to the presence of the protein-PVP copolymer.

In this specification the following test methods have been used:

1) Particle Size Measurement of Primary Titanium Dioxide Particles

A small amount of titanium dioxide, typically 2 mg, was pressed into approximately 2 drops of an oil, for one or two minutes using the tip of a steel spatula. The resultant suspension was diluted with solvent and a carbon-coated grid suitable for transmission electron microscopy was wetted with the suspension and dried on a hot-plate. Approximately 18 cm×21 cm photographs were produced at an appropriate, accurate magnification. Generally about 300-500 crystals were displayed at about 2 diameters spacing. A minimum number of 300 primary particles were sized using a transparent size grid consisting of a row of circles of gradually increasing diameter, representing spherical crystals. Under each circle a series of ellipsoid outlines were drawn representing spheroids of equal volume and gradually increasing eccentricity. The basic method assumes log normal distribution standard deviations in the 1.2-1.6 range (wider crystal size distributions would require many more crystals to be counted, for example of the order of 1000). The suspension method described above was suitable for producing almost totally dispersed distributions of primary metal oxide particles whilst introducing minimal crystal fracture. Any residual aggregates (or secondary particles) were sufficiently well defined that they, and any small debris, could be ignored, and effectively only primary particles included in the count. Mean length, mean width and length/width size distributions of the primary titanium dioxide particles were calculated from the above measurements.

2) Median Particle Volume Diameter and Particle Size Distribution of Titanium Dioxide Particles in Dispersion A dispersion of titanium dioxide particles was produced by mixing 6.3 g of polyhydroxystearic acid with 48.7 g of C12-C15 alkylbenzoate, and then adding 45 g of titanium dioxide into the solution. The mixture was passed through a horizontal bead mill, operating at approximately 2100 r.p.m. and containing zirconia beads as grinding media for 15 minutes. The dispersion of titanium dioxide particles was diluted to between 30 and 40 g/l by mixing with isopropyl myristate. The diluted sample was analysed on the Brookhaven BI-XDC particle sizer in centrifugation mode, and the median particle volume diameter and particle size distribution measured.

3) Molecular Weight of Protein and Protein-PVP Copolymer

Molecular weight (weight average) was determined by size exclusion HPLC using the following methodology;

| | |
|---|---|
| Column | TSK-GEL GMPWxl (30 cm × 7.8 mm internal diameter) |
| Guard column | TSK PWxl (4 cm × 6 mm internal diameter) |
| Pump | HP1100 series isocratic pump (G1310A) |
| Injector | HP1100 series autosampler (G1313A) |
| Thermostat | HP1100 series thermostated column compartment (G1316A) |
| Detector | HP1100 series variable wavelength detector (G1314A) |
| Control | HP1100 series Chemstation software (G2175A) |
| Integration | Polymer Laboratories Cirrus GPC software |
| Eluent | 0.04M $KH_2PO_4$, 0.05M $K_2HPO_4 \cdot 3H_2O$ and 0.08M sodium chloride (800 ml) plus acetonitrile(200 ml) adjusted to pH 7.0 |

-continued

| | |
|---|---|
| Flow rate | 0.6 ml per minute |
| Injection volume | 5 μl |
| Temperature | 40° C. |
| Wavelength | 220 nm |
| Standards | Sodium polystyrene sulphonate standards of known molecular weight. 10 standards were used in the range 5,000 to 800,000 Daltons. |
| Calibration fit type | First order polynomial (linear) |
| Fit ratio | 1.00 ± 0.02 |

4) Sun Protection Factor

The in vitro Sun Protection Factor (SPF) of a sunscreen formulation (e.g. as in Examples 3, 4 and 5) was determined using the method of Diffey and Robson, J. Soc. Cosmet. Chem. Vol. 40, pp 127-133, 1989.

The invention is illustrated by the following non-limiting examples.

EXAMPLE 1

500 g of an aqueous solution of alkali hydrolysed wheat protein (20% by weight) having a molecular weight (weight average) of 80,000 Daltons and 688 g of water were mixed in a beaker. 2.4 g of 25% sodium hydroxide was added to increase the pH to 8. The liquor was transferred to a flange flask which was fitted with a condenser and sealed. 303 g of 1-vinyl-2-pyrrolidone were added. The flask was then transferred to a water bath where it was heated to 70° C. A solution of 19.7 g of V50 initiator (azobis(amidinopropane) dihydrochloride) in 180 g of water was prepared, and gradually added to the flask over 1 hour. Once the addition was complete, the reaction was allowed to proceed for a further 3 hours. The pH was then lowered to 5.8 by the addition of hydrochloric acid. The resulting liquor was filtered to give a clear yellow aqueous solution containing approximately 25% by weight of hydrolysed wheat protein-PVP copolymer having a molecular weight (weight average) of 100,000 Daltons.

EXAMPLE 2

The general process of Example 1 was repeated except that 750 g of an aqueous solution of enzyme hydrolysed wheat protein (20% by weight) having a molecular weight (weight average) of 2000 Daltons and 509 g of 1-vinyl-2-pyrrolidone were used. The resulting clear yellow aqueous solution contained approximately 20% by weight (2627 g) of hydrolysed wheat protein-PVP copolymer having a molecular weight (weight average) of 40,000 Daltons.

EXAMPLE 3

The hydrolysed wheat protein-PVP copolymer solution produced in Example 2 was used to prepare an oil-in-water sunscreen emulsion having the following composition;

| | % w/w |
|---|---|
| Phase A. | |
| DC 245 Fluid (Cyclopentasiloxane) | 8.0 |
| CRODAMOL ™ OP (Ethylhexyl Palmitate (ex Croda)) | 5.0 |
| DC 2502 Fluid (Cetyl Dimethicone) | 2.0 |
| ARLAMOL ™ HD (Isohexadecane (ex Croda)) | 2.5 |

-continued

| | % w/w |
|---|---|
| CRODAMOL ™ AB (C12-15 Alkyl Benzoate (ex Croda)) | 2.5 |
| TIOVEIL ™ 50 FIN (C12-15 Alkyl Benzoate (&) Titanium Dioxide (&) Polyhydroxystearic Acid (&) Aluminium Stearate (&) Alumina (ex Croda)) Phase B. | 10.0 |
| Water | qs |
| ARLATONE ™ 2121 (Sorbitan Stearate (&) Sucrose Cocoate (ex Croda)) | 4.5 |
| Keltrol RD (Xanthan Gum) | 0.2 |
| Veegum Ultra (Magnesium Aluminium Silicate) | 0.8 |
| Rewoderm S1333 (Disodium Ricinoleamido MEA-Sulfosuccinate) | 0.2 |
| D-Panthenol | 0.8 |
| Propylene Glycol Phase C. | 4.0 |
| Hydrolysed Wheat Protein-PVP Copolymer produced in Example 2 | 2.0 |
| Phenonip | 0.4 |

Procedure

1. Arlatone™ 2121 and water were mixed together and heated to 80° C. until fully dispersed.
2. The remaining aqueous Phase B ingredients were added whilst maintaining temperature at 80° C.
3. The oil Phase A ingredients were mixed together and heated to 75-80° C.
4. Phase A was added to Phase B with intensive stirring.
5. The mixture was homogenised for 2 minutes.
6. The mixture was stirred and cooled to room temperature, with the Phase C ingredients being added below 40° C.

The sunscreen product had an in vitro SPF value of 14.5, compared to 8.8 for the same formulation containing no hydrolysed wheat protein-PVP. This is a 60.7% increase in the SPF value of the formulation.

EXAMPLE 4

The hydrolysed wheat protein-PVP copolymer solutions produced in Examples 1 and 2 were used to prepare an oil-in-water sunscreen emulsions having the following composition;

| | % w/w |
|---|---|
| Phase A. | |
| PRISORINE ™ 2039 (Isopropyl Isostearate (ex Croda)) | 4.0 |
| CRODAMOL ™ OP (Ethylhexyl Palmitate (ex Croda)) | 1.9 |
| ARLAMOL ™ HD (Isohexadecane (ex Croda)) | 7.0 |
| PRIPURE ™ 3759 (Squalane (ex Croda)) | 8.0 |
| SOLAVEIL ™ CT-100 (C12-15 Alkyl Benzoate (&) Titanium Dioxide (&) Aluminium Stearate (&) Polyhydroxystearic Acid (&) Alumina (ex Croda)) Phase B. | 12.5 |
| Water | qs |
| ARLATONE ™ 2121 (Sorbitan Stearate (&) Sucrose Cocoate (ex Croda)) | 4.5 |
| Keltrol RD (Xanthan Gum) | 0.2 |
| Veegum Ultra (Magnesium Aluminium Silicate) | 0.8 |
| Rewoderm S1333 (Disodium Ricinoleamido MEA-Sulfosuccinate) | 0.2 |
| D-Panthenol | 0.8 |
| Propylene Glycol Phase C. | 4.0 |
| Hydrolysed Wheat Protein-PVP Copolymer produced in Examples 1 or 2 | 2.0 |
| Phenonip | 0.4 |

The sunscreen products were produced using a similar procedure as described in Example 3. The in vitro SPF values for the compositions containing the hydrolysed wheat protein-PVP were 24.3 (for Example 1 material) and 23.2 (for Example 2 material), compared to 14.2 for the same formulation containing no hydrolysed wheat protein-PVP. These are 71.1% (Example 1) and 63.4% (Example 2) increases in the SPF value of the formulation.

EXAMPLE 5

The hydrolysed wheat protein-PVP coolymer solution produced in Example 2 was used to prepare an oil-in-water sunscreen emulsion having the following composition;

|  | % w/w |
|---|---|
| Phase A. | |
| ARLACEL ™ 165 FL (Glyceryl Stearate (&) PEG-100 Stearate (ex Croda)) | 6.0 |
| SPAN ™ 60 (Sorbitan Stearate (ex Croda)) | 0.5 |
| TWEEN ™ 60V (Polysorbate 60 (ex Croda)) | 0.9 |
| CRODACOL ™ S95 EP (Cetearyl Alcohol (ex Croda)) | 1.0 |
| Light Mineral Oil | 8.0 |
| Dow Corning 200 Fluid (350 cst) | 2.0 |
| CRODAMOL ™ OP (Ethylhexyl Palmitate (ex Croda)) | 5.0 |
| Escalol 557 (Ethylhexyl Methoxycinnamate (ex ISP) | 5.0 |
| Tinosorb S (Bis-Ethylhexyloxyphenol Methoxyphenyl Triazine (ex Ciba) | 2.0 |
| Phase B. | |
| Water | qs |
| Keltrol RD (Xanthan Gum) | 0.1 |
| Propylene Glycol | 4.0 |
| Phase C. | |
| Hydrolysed Wheat Protein-PVP Copolymer produced in Example 2 | 2.0 |
| Germaben II | 1.0 |

The sunscreen product was produced using a similar procedure as described in Example 3, and had an in vitro SPF value of 26.9, compared to 18.0 for the same formulation containing no hydrolysed wheat protein-PVP. This is a 49.4% increase in the SPF value of the formulation.

EXAMPLE 6

The hydrolysed wheat protein-PVP coolymer solution produced in Example 2 was used to prepare a low viscosity sprayable emulsion having the following composition;

|  | % w/w |
|---|---|
| Phase A. | |
| ARLACEL ™ 165 FL (Glyceryl Stearate (&) PEG-100 Stearate (ex Croda)) | 1.5 |
| SPAN ™ 60 (Sorbitan Stearate (ex Croda)) | 1.0 |
| ARLAMOL ™ HD (Isohexadecane (ex Croda)) | 1.5 |
| CRODAMOL ™ AB (C 12-15 Alkyl Benzoate (ex Croda)) | 3.0 |
| CRODAMOL ™ OC (Ethylhexyl Cocoate) | 3.0 |
| Dow Corning 245 Fluid (Cyclopentasiloxane) | 2.25 |
| Escalol 557 (Ethylhexyl Methoxycinnamate (ex ISP)) | 6.0 |
| Eusolex OCR (Octocrylene (ex Merck)) | 6.0 |
| Parsol 1789 (Butyl Methoxydibenzoylmethane, ex DSM)) | 4.0 |
| Titriplex III (Disodium EDTA) | 0.1 |
| Phase B. | |
| Water | qs |
| Keltrol RD (Xanthan Gum) | 0.1 |

-continued

|  | % w/w |
|---|---|
| Veegum Ultra (Magnesium Aluminium Silicate ) | 0.4 |
| CRODAFOS ™ MCK (Potassium Cetyl Phosphate, ex Croda) | 3.0 |
| CRODEROL ™ GV9000 (Glycerin, ex Croda) | 3.0 |
| SOLAVEIL ™ CT-10W (Aqua (and) Titanium Dioxide (and) Isodeceth-6 (and) Oleth-10 (and) Aluminum Stearate (and) Alumina (and) Simethicone, ex Croda) | 12.5 |
| Phase C. | |
| Hydrolysed Wheat Protein-PVP Copolymer produced in Example 2 | 2.0 |
| Preservative | qs |

Procedure
1. Keltrol RD and Veegum Ulta were dispersed into the water, the remaining water Phase B ingredients were added, and the mixture heated to 75-80° C.
2. Solaveil CT-10W was added to water Phase B with stirring, whist maintaining temperature.
3. Oil Phase A ingredients were mixed together and heated to 75-80° C.
4. Phase A was added to Phase B with stirring, and homogenised for 1 minute.
5. The mixture was stirred and cooled to room temperature, with the Phase C ingredients being added below 40° C.

The sunscreen product had an in vivo SPF value (measured by proDERM, Germany) of 56, compared to 41.6 for the same formulation containing no hydrolysed wheat protein-PVP. This is a 34.6% increase in the SPF value of the formulation.

The above examples illustrate the improved properties of a composition according to the present invention.

The invention claimed is:
1. A sunscreen emulsion composition, comprising:
   i) an oil phase comprising at least one of:
      a) 1-20 wt. % of an organic sunscreen, based on the total weight of the sunscreen emulsion composition; and
      b) 2-12 wt. % of titanium dioxide particles, based on the total weight of the sunscreen emulsion composition, wherein said titanium dioxide particles have a hydrophobic coating and have a median volume particle diameter of 24 to 42 nm; and
   ii) an aqueous phase comprising 0.2-1 wt. %, based on the total weight of the sunscreen emulsion composition, of a protein-polyvinylpyrrolidone (PVP) copolymer having a protein to PVP ratio in the range of 5-70:30-95 wt. %;
   wherein the sunscreen emulsion composition:
   1) has an SPF value of greater than 10; and
   2) has an increase in SPF value of greater than 8% per 0.1 wt. % of protein-PVP copolymer present in said sunscreen emulsion composition, relative to said sunscreen emulsion composition exclusive of the protein-PVP copolymer.

2. The emulsion composition of claim 1, wherein the organic sunscreen is selected from the group consisting of butyl methoxydibenzoylmethane, ethylhexyl methoxycinnamate, octocrylene, and mixtures thereof.

3. The emulsion composition of claim 1, wherein the titanium dioxide particles are dispersed in a dispersing agent.

4. The emulsion composition of claim 1, wherein the increase in the SPF value due to the presence of the protein-PVP copolymer is greater than 20%.

5. The emulsion composition of claim 1, wherein the emulsion composition comprises 0.3-0.5 wt. % of the protein-PVP copolymer.

6. The emulsion composition of claim 1, wherein the emulsion composition comprises 0.4 wt. % of the protein-PVP copolymer.

7. The emulsion composition of claim 1, wherein the SPF increase is obtainable at a concentration of 0.4 wt. % of the protein-PVP copolymer.

8. The emulsion composition of claim 1, wherein the sunscreen emulsion composition has an SPF value in the range of between 20-100.

9. The emulsion composition of claim 1, wherein the oil phase comprises both said organic sunscreen and said titanium dioxide particles.

10. The emulsion composition of claim 3, wherein the dispersing agent is polyhydroxystearic acid.

11. A method of improving sunscreen effectiveness, comprising combining a protein-PVP copolymer and sunscreen in an emulsion composition, wherein the improved sunscreen effectiveness is an increase in SPF value of greater than 8% per 0.1 wt. % of the protein-PVP copolymer present in said emulsion composition, relative to said emulsion composition exclusive of the protein-PVP copolymer, wherein the sunscreen comprises titanium dioxide particles having a hydrophobic coating, and wherein the emulsion composition is a sunscreen emulsion composition according to claim 1.

12. The method of claim 11, wherein the emulsion composition contains 2-40 wt. % of sunscreen incorporated into the oil phase of the emulsion composition based on the total weight of the emulsion composition.

13. The method of claim 12, wherein the sunscreen comprises both the titanium dioxide particles and an organic sunscreen.

14. The method of claim 13, wherein the organic sunscreen is selected from the group consisting of butyl methoxydibenzoylmethane, ethylhexyl methoxycinnamate, octocrylene, and mixtures thereof.

15. The method of claim 12, wherein the sunscreen in the oil phase comprises 2-20 wt. % of a metal oxide sunscreen, based on the total weight of the emulsion composition.

16. The method of claim 11, wherein the increase in the SPF value of the emulsion composition containing the added protein-PVP copolymer is greater than 20%, relative to said emulsion composition exclusive of the protein-PVP copolymer.

* * * * *